(12) United States Patent
Gabriel et al.

(10) Patent No.: US 6,461,858 B1
(45) Date of Patent: Oct. 8, 2002

(54) ENZYME ACTIVATED SUPPORTS FOR ENANTIOMERIC SEPARATIONS

(75) Inventors: Richard L. Gabriel, Swampscott; David A. Swanson, Lexington, both of MA (US)

(73) Assignee: Pharm-Eco Laboratories, Inc., Devens, MA (US)

(*) Notice: Subject to any disclaimer, the term of this patent is extended or adjusted under 35 U.S.C. 154(b) by 0 days.

(21) Appl. No.: 09/237,334

(22) Filed: Jan. 26, 1999

Related U.S. Application Data

(60) Provisional application No. 60/072,442, filed on Jan. 26, 1998.

(51) Int. Cl.[7] .................................................. C07C 1/00
(52) U.S. Cl. ...................... 435/280; 210/640; 210/660; 210/661; 210/662
(58) Field of Search ..................... 435/280; 210/635, 210/656, 198.2, 502 D, 640, 660, 661, 662

(56) References Cited

U.S. PATENT DOCUMENTS

| | | | |
|---|---|---|---|
| 4,108,723 A | | 8/1978 | Hirohara et al. ............... 195/2 |
| 4,439,524 A | | 3/1984 | Schutt .......................... 435/280 |
| 4,800,162 A | * | 1/1989 | Matson ....................... 435/280 |
| 5,021,345 A | | 6/1991 | Urban et al. ................. 435/180 |
| 5,078,886 A | * | 1/1992 | Hsu ............................ 210/632 |
| 5,518,625 A | | 5/1996 | Priegnitz et al. ............. 210/659 |
| 5,626,762 A | | 5/1997 | Priegnitz et al. ............. 210/659 |
| 5,645,729 A | | 7/1997 | Priegnitz et al. ............. 210/659 |
| 6,027,648 A | * | 2/2000 | Haginaka et al. ........... 210/635 |

FOREIGN PATENT DOCUMENTS

| | | |
|---|---|---|
| EP | 0 182 517 A2 | 5/1986 |
| EP | 0 214 569 A2 | 3/1987 |
| EP | 0 330 217 A2 | 8/1989 |
| EP | 0 407 033 A2 | 1/1991 |
| EP | 0 461 043 A2 | 12/1991 |
| EP | 0 657 544 A1 | 6/1995 |
| JP | 3 191 797 | 8/1991 |
| JP | 7 067 692 | 3/1995 |
| WO | WO 91 13163 | 9/1991 |
| WO | WO 92 14743 | 9/1992 |

OTHER PUBLICATIONS

Gattuso, M.J., et al., "Simulated Moving Bed Technology –the Perparation of Single Enantiomer Drugs," *Chemistry Today:* 17–20 (Nov./Dec. 1996).

Johnson, J.A. and Kabza, R.G., "Sorbex: Industrial–Scale Adsorptive Separation," *Preparative and Industrial Scale Chromatography*, G. Ganetsos and P.E. Barker, eds., Chap. 12:257–271 (1993).

* cited by examiner

*Primary Examiner*—David A. Redding
(74) *Attorney, Agent, or Firm*—Hamilton, Brook, Smith & Reynolds, P.C.

(57) ABSTRACT

An enzyme is immobilized on a solid support and can react selectively with one enantiomer in an enantiomeric mixture. A methods of using the enzyme immobilized solid support in conjunct with a separating means to separate enantiomeric mixtures is described. An apparatus for separating an enantiomeric mixture using an enzyme immobilized on a solid support is also described.

11 Claims, 1 Drawing Sheet

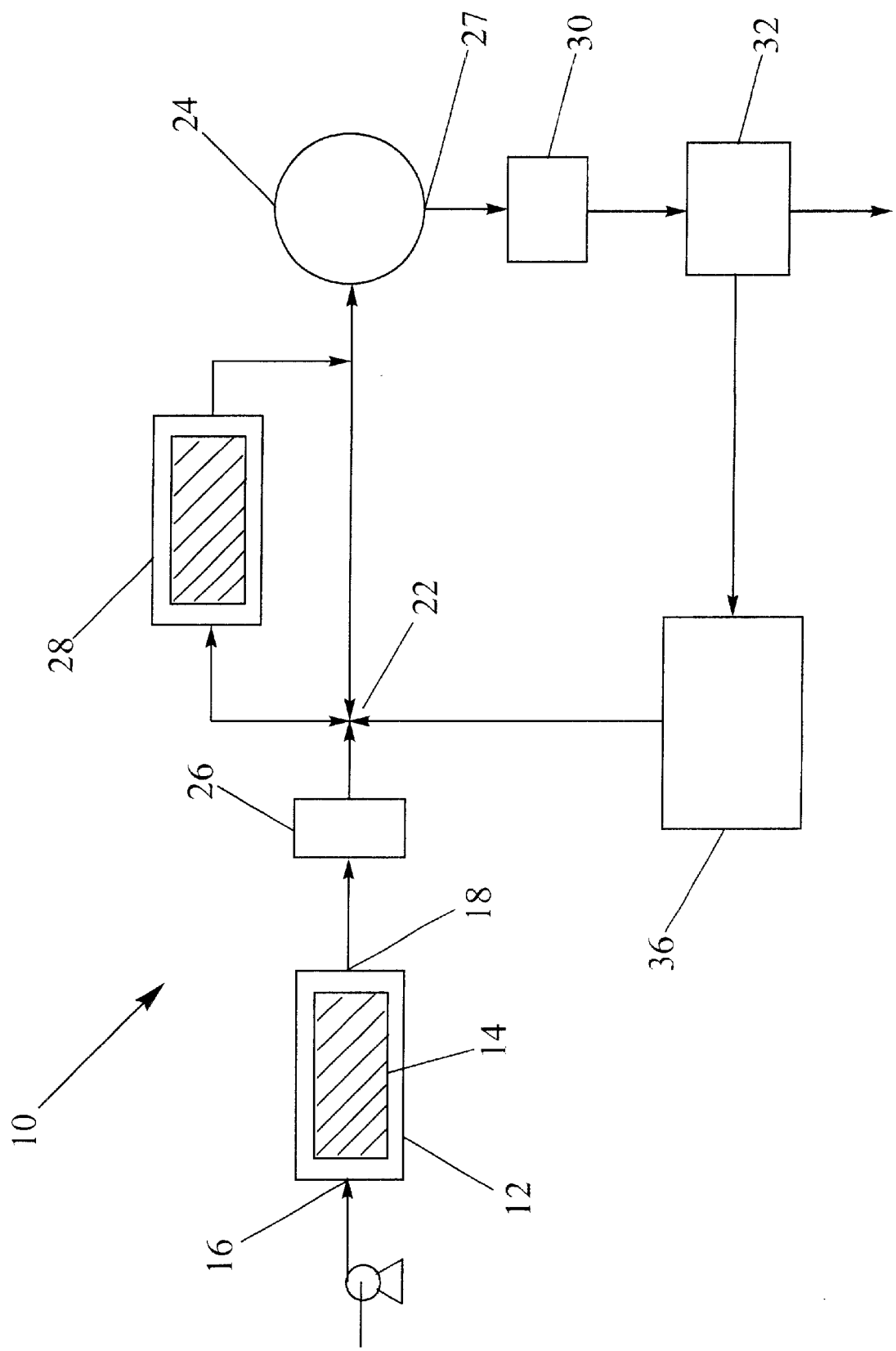

ENZYME ACTIVATED SUPPORTS FOR ENANTIOMERIC SEPARATIONS

RELATED APPLICATION

This application claims the benefit of U.S. Provisional Application No. 60/072,442, filed on Jan. 26, 1998, entitled "Enzyme Activated Supports for Enantiomeric Separations" the entire teachings of which are incorporated herein by reference.

BACKGROUND OF THE INVENTION

Strategies to obtain a single enantiomer of a compound have become important in drug discovery because often one enantiomer is an effective drug while the other enantiomer has undesirable biological activity. Ideally, an asymmetric synthesis is designed to produce only the desired enantiomer. Unfortunately, more often than not, an asymmetric synthesis cannot be designed or is prohibitively expensive.

Alternatively, the mixture of enantiomers can be separated. However, mixtures of enantiomers are difficult, and often impossible, to separate because the physical properties of the enantiomers are identical towards achiral substances and can only be distinguished by their behavior towards other chiral substances. Chromatographic methods using a chiral solid phase have been utilized to separate enantiomeric mixtures, but chiral solid supports are expensive and, typically, the resolution is poor.

An alternative method of separating enantiomeric mixtures is by reacting them with a chiral reagent. In this procedure, the mixture of enantiomers react with the chiral reagent to form diastereomers which are distinguishable from each other on the basis of their properties towards achiral substances, and therefore, can be separated by techniques such as recrystallization or chromatography. This process is time consuming and results in loss of yield because it requires two additional reaction steps (i.e., one reaction to add the chiral auxiliary to the enantiomers and another reaction to remove it after the diasteriomers have been separated).

In some instances, a chiral reagent will react much faster with one enantiomer than with the other enantiomer in the enantiomeric mixture. In this case, the enantiomer which reacts faster can be removed before the other enantiomer is formed. This method also necessitates two additional reaction steps to add the chiral auxiliary and to remove it after the separation.

The methods described above cannot always be applied successfully to a particular system, and when they can be applied, they are often expensive, time consuming and results in loss of yield. Therefore, the need exists for new methods of obtaining a single enantiomer from an enantiomeric mixture.

SUMMARY OF THE INVENTION

One embodiment of the present invention is a solid support bonded to an enzyme which selectively reacts with one enantiomer in an enantiomeric mixture.

Another embodiment of the present invention is a method of selectively reacting one enantiomer in an enantiomeric mixture. The method comprises contacting the enantiomeric mixture with an enzyme which: 1) is bonded to a solid support; and 2) selectively reacts with one enantiomer, called the "reactive enantiomer," in the enantiomeric mixture to form a derivative of the reactive enantiomer. The immobilized enzyme and enantiomeric mixture are contacted under conditions suitable for reacting the immobilized enzyme and the reactive enantiomer, thereby forming a product mixture comprising the unreactive enantiomer and a derivative of the reactive enantiomer.

Another embodiment is a method of separating a derivative of one enantiomer from an enantiomeric mixture. The method involves contacting the enantiomeric mixture with an enzyme which: 1) is bonded to a solid support; and 2) selectively reacts with one enantiomer in the enantiomeric mixture to form a derivative of the reactive enantiomer. The immobilized enzyme and enantiomeric mixture are contacted under conditions suitable for reacting the immobilized enzyme and the reactive enantiomer, thereby forming a product mixture comprising the unreactive enantiomer and a derivative of the reactive enantiomer. The product mixture is then treated with a separating means to separate the derivative of the reactive enantiomer from the unreacted enantiomer.

Another embodiment is an apparatus for obtaining a derivative of one enantiomer in an enantiomeric mixture. The apparatus has a reaction chamber which contains an enzyme immobilized on a solid support, a means of delivering solvent to the reaction chamber, a means of loading a sample into the reaction chamber and a vessel for collecting a sample as it exits the reaction chamber.

Reported herein is the discovery of a solid support and a method for separating a single enantiomer from an enantiomeric mixture which eliminates the need to derivatize the chiral compound with a chiral auxiliary before separating the enantiomers and does not require the use of expensive chiral solid supports.

BRIEF DESCRIPTION OF THE DRAWING

The FIGURE is a schematic depiction of an apparatus for obtaining a derivative of one enantiomer from an enantiomeric mixture.

DETAILED DESCRIPTION OF THE INVENTION

The features and other details of the method of the invention will now be more particularly described and pointed out in the claims. It will be understood that the particular embodiments of the invention are shown by way of illustration and not as limitations of the invention. The principle features of this invention can be employed in various embodiments without departing from the scope of the invention. All parts and percentages are by weight unless otherwise specified.

In one embodiment the invention is a solid support bound to an enzyme which can react selectively with one enantiomer in an enantiomeric mixture. An "enantiomeric mixture" comprises an enantiomer and its optical isomer. An enantiomeric mixture can be racemic, i.e., comprises equimolar amounts of each enantiomer. Alternatively, an enantiomeric mixture can have an excess of one enantiomer. In addition, a enantiomeric mixture can contain additional components which do not substantially interfere with the enzymatic reaction.

Suitable enzymes for use with the present invention are those which 1) react at a faster rate with one enantiomer in an enantiomeric solution than with the other enantiomer; and 2) retain at least some of their activity when attached to a solid support can be used in the present invention. Suitable enzymes include but are not limited to proteases, glycosidases, esterases, lipases, alcohol dehydrogenases, alcohol oxidases, glucose dehydrogenases, glucose oxidases, albumin, a luciferases, asparaginases, nicotinamide adenine dinucleotide, flavin adenine dinucleotide, and an ureases. Carboxypeptidase A, chymotrypsin, trypsin, elastase and subtilisin are preferred proteases. Lysozyme is a preferred glycosidase. Pig liver esterase and porcine liver esterase are preferred esterases.

The type of solid support used is not critical to the invention. Therefore, any solid support can be utilized provided that an enzyme can be immobilized on it such that it still retains some of its activity. Examples of suitable solid supports include semi-permeable membranes, glass capillaries, alumina, alumina supported polymers, silica, chemically bonded hydrocarbons on silica, polyolefins, agarose, polysaccharides such as dextran, or glycoproteins such as fibronectin. Preferably, the solid support is in the form of particles. A particularly preferred solid support is IPS 400, an alumina support polymer; specifically, macroreticular aluminum oxide support, marketed under the name Hysurf, by UOP, LLC.

In one embodiment, the method of the invention includes reacting an enzyme with a functional group on the solid support directly, or by forming an activated solid support by reacting the solid support with a bifunctional linker that can react with both the solid support and the enzyme. Examples of suitable bifunctional linkers include dialdehydes, dimethyl adipimidate, dimethylsuberimidate, hexamethylenediisocyanate, hexamethylenediisothiocyanate, 3-(2-pyridyldithio)propionic acid N-hydroxysuccininmide ester, glutathione, and cyanogen bromide. Typically, a solid support is treated with the bifunctional linker under conditions wherein the bifunctional linker reacts with a functional group on the solid support forming a derivatized solid support. The solid support is then washed with solvent to remove any bifunctional linker that did not bind to the solid support. The enzyme is suspended in a suitable solvent which does not significantly diminish the activity of the enzyme. Examples include water, aqueous buffers, organic solvents or combinations thereof, depending on the type of enzyme being used. The dissolved enzyme is then combined with the derivatized solid support and stirred for a sufficient length of time to allow the enzyme to become bonded to the support, e.g., up to sixteen hours.

In another embodiment, the method of the invention includes a reaction between the immobilized enzyme and the enantiomeric mixture that can be carried out in any suitable reaction vessel, for example a plug flow reactor, membrane reactor, beaker, a micro well and the like. The reaction can be carried out in solvents which do not significantly diminish the activity of the enzyme and which dissolves the enantiomers. Examples include aqueous solvents, buffered aqueous solvents, organic solvents and combinations thereof, depending upon the enzyme and substrates being used.

In another embodiment, the invention is directed to obtaining one enantiomer or a derivative of one enantiomer from an enantiomeric mixture. An example of an apparatus for obtaining one enantiomer or a derivative of one enantiomer from an enantiomeric mixture is shown in the FIGURE. An enantiomeric mixture, such as a racemic mixture, is contacted with an activated enzyme support (i.e., a solid support that is bound to an enzyme that reacts selectively with one enantiomer in an enantiomeric mixture, as described above.)

After the reaction, the product mixture can be separated from the immobilized enzyme by any suitable means, for example, by filtration. The product mixture can be then analyzed to determine the relative amounts of each enantiomer remaining and the relative amounts of product obtained from each enantiomer. The analysis is carried out by any suitable means, including by measuring the optical rotation of the product mixture with a chiral detector as in the FIGURE or by chiral chromatography (e.g., HPLC with a chiral column).

Alternatively, the product mixture can be sent directly to a separation means after the immobilized enzyme has been removed. A "separation means" is a device which is suitable for separating the unreactive enantiomer from the reaction product of its optical isomer. Examples of separating means include a recrystallization apparatus, an extraction apparatus, a precipitation apparatus, an electrophoresis apparatus, or a chromatography apparatus such as a thin layer chromatography apparatus, a paper chromatography apparatus, a reversed phase chromatography column, a normal phase chromatography column, an ion-exchange chromatography column, a gas chromatography column and an affinity chromatography column. Preferred separation means are reversed phase chromatography columns, normal phase chromatography columns, ion-exchange chromatography columns, gas chromatography columns and affinity chromatography columns. A single chromatography column can be utilized for the separation or, alternatively, a series of columns can be used. A particularly preferred separating means is a simulated moving bed (hereinafter "SMB") apparatus. SMB is a technique that allows the separation of products from partially resolved chromatographic profiles. The product to be separated is fed into the midpoint of a column and allowed to spread out to form a concentration profile. The profile is maintained in place by moving the stationary phase in the opposite direction as the mobile phase. Pure product is withdrawn from the edges of the concentration profile. SMB has been described in Gattuso, et al., *Chemistry Today*, (1996), 17; J. A. Johnson, et al., *Preparative and Industrial Scale Chromatography* (1993), 61:257; D. B. Broughton, *Chem. Eng. Prog.* (1968), 68:6, and in U.S. Pat. Nos. 5,518,625, 5,626,762, and 5,645,729, the teachings of which are incorporated herein by reference.

In yet another alternative, the product mixture can be reacted with the same immobilized enzyme or with fresh immobilized enzyme. This embodiment is preferred if the mixture has been analyzed, for example by a chiral detector, and found to contain unreacted starting material.

An apparatus of the invention is shown schematically in the FIGURE. Apparatus 10 includes reaction vessel 12 containing activated solid support 14. Vessel 12 has solvent inlet 16 and solvent outlet 18 that are each plugged with a porous material which allows solvent to flow into and out of the vessel but does not allow activated solid support 14 to escape from the vessel. The type of porous material is not critical to the invention provided it is inert under the conditions use for reacting the enzyme with the reactive enantiomer, and it has a pore size that is less than the particle diameter of the activated solid support. Sintered glass, polymeric membranes or metallic sieves are typical porous materials.

An enantiomeric mixture is dissolved in a suitable solvent (aqueous, organic or a combination thereof) which does not significantly diminish the activity of the enzyme and allowed to flow through reaction vessel 12 at a rate to control the desired conversion. The means for feeding a solvent into reaction vessel 12 include pump pressure from a compressed inert gas or gravity. The sample can be introduced into reaction vessel 12 by an injector (not shown) placed upstream of reaction vessel 12. Alternatively, a sample can be introduced into the reaction vessel by absorbing the sample onto a solid support and allowing the solvent to flow over the solid support into the reaction vessel.

Outlet 18 of the reaction vessel 12 can be connected to a sample collector or it can be connected by, for example, four-way valve 22, to separation means 24. Preferably, the outlet 18 of reaction vessel 12 is connected to chiral detector 26, where the net optical rotation is used to determine the presence of any unconverted reactive enantiomer. Chiral detector 26 is a detector that uses the properties of plane polarized light or other means of detecting the chiral purity of the mixture. If unconverted reactive enantiomer is detected, the stream is sent back through reaction vessel 12 or to another reaction vessel 28, and then to separation means 24. If no unconverted enantiomer is detected, the stream is sent directly to separation means 24. Outlet 27 of separation means 24 is connected to detector 30. Suitable detectors include ultraviolet light detectors or refractive index detectors. Sample collection container 32 can be connected to an outlet of detector 30 to collect the sample. A preferred sample collector is a fraction collector. The sample or portions of the sample can then be processed further to recover product, starting materials, recycle solvents, recycle components back to the activated support column or continue for further processing.

Eluent collected from separation means 24 in sample collector 32, includes an alcohol fraction and a fraction containing the enanteromeric mixture. The enantiomeric mixture can be racemized in a separate vessel 36 before sending it back through reaction vessel 28. Racemization techniques are known to those skilled in the art (see, for example, March, *Advanced Organic Chemistry*, (1985)). Typically the chiral compound is racemized by treating it with an acid, a base or a catalyst.

EXEMPLIFICATION

EXAMPLE 1
Formation of a Derivatized Solid Support

An aqueous solution (11.4 g) containing 25% glutaric dialdehyde was diluted with water (102.6 g). IPS 400 macroreticular aluminum oxide solid support (10.0 g) was added to the glutaric dialdehyde solution and the mixture was allowed to stand at room temperature for 70–80 min. The glutaric dialdehyde solution was decanted off and the derivatized IPS 400 macroreticular aluminum oxide solid support was washed with 10×200 mL of water. Excess water was removed by vacuum filtration. The derivatized IPS 400 macroreticular aluminum oxide solid support weighed 11.76 g.

EXAMPLE 2
Immobilization of Pig Liver Esterase on Derivatized Solid Support to Form an Activated Solid Support A pH 7–8 buffer (hereinafter "immobilization buffer") is prepared by dissolving 2.2 g sodium dihydrogen phosphate monohydrate and 8.2 g potassium hydrogen phosphate dibasic in 210 mL water. 46.2 mL of a solution of pig liver esterase (65 mg/mL) was combined with 27.9 mL of the immobilization buffer. 11.76 g of the derivatized IPS 400 macroreticular aluminum oxide solid support was added to the solution of pig liver esterase, and the mixture was stirred gently every 15–20 min. for 16 h. The pig liver esterase solution was decanted, and the activated solid support was washed with 4×40 mL of the immobilization buffer. The amount of pig liver esterase loaded on the solid support was 122 mg/g of solid support.

EXAMPLE 3
Immobilization of Porcine Liver Esterase on Derivatized Solid Support Lyophilized porcine liver esterase was dissolved in 196 mL of immobilization buffer. Approximately 29.4 g of IPS 400 macroreticular aluminum oxide derivatized solid support made by the method described in Example 1 was added to the porcine liver esterase solution and stirred occasionally for 4 h and 10 min. The porcine liver esterase solution was decanted and the activated solid support was washed with 4×200 mL of immobilization buffer and 4×200 mL of water.

EXAMPLE 4
Selective Conversion of cis-(+)-[5-(Amino-5-Fluoro-2-Oxo-1(2H)-Pyrimidineyl)-1,3-Oxathiolan-2-yl]methylbutanoate (hereinafter "ester") to cis-(+)-[5-(Amino-5-Fluoro-2-Hydroxy-1(2H)-Pyrimidineyl)-1,3-Oxathiolan-2-yl]methylbutanoate (hereinafter "alcohol") in the Presence of (−) Ester The activated solid support made in Example 3 was loaded into a 6×2.21 cm column and was washed overnight with a 50/50 mixture of immobilization buffer and water. After the washing step was complete, the column containing activated solid support was aligned in series on an HPLC system with a C18 column (ZORBAX® LP 100/40). 20 μL of a racemic mixture of a chiral ester was pumped through the activated solid support column where the (+) ester was converted to the (+) alcohol. Then the sample was pumped through a C18 column to separate the (−) ester as a function of flow and any remaining (+) ester from the (+) alcohol. The amount of conversion of the (+) ester can be controlled by the rate at which the sample is pumped through the activated column (see Table 1). Conversion of the ester group to an alcohol significantly changes the affinity of the compound for the C18 solid support so the ester can easily be separated from the (+) alcohol product. Therefore, the (+) enantiomer of the alcohol can be obtained without using of a column having a chiral stationary phase.

TABLE 1

Results of conversion of (+) ester of a racemic mixture to (+) alcohol on an activated solid support column followed by separation of the (+) alcohol from the (±) ester

| Sample | (±) Ester | (±) Alcohol | Flow Rate |
| --- | --- | --- | --- |
| initial | 98.0% | 1.1% | NA |
| 1 | 91.75% | 8.11% | 1 mL/min. |
| 2 | 81.82% | 15.66% | 0.5 mL/min. |

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. An enzyme activated support for selective conversion of one enantiomer in an enantiomeric mixture, comprising;
   a) a solid support in the form of particles and composed of a material selected from the group consisting of glass capillaries, alumina, silica, a chemically bonded hydrocarbon on silica, a polyolefin, agarose, a polysaccharide, or a glycoprotein; and
   b) lysozyme, wherein said lysozyme selectively reacts with one enantiomer in an enantiomeric mixture, and wherein said lysozyme is bound to the support.

2. A method of separating a derivative of one enantiomer from an enantiomeric mixture, comprising the steps of:

a) contacting said enantiomeric mixture with an enzyme selected from pig liver esterase or porcine liver esterase which:
  i) is bound to a solid support, wherein the solid support is in the form of particles and composed of a material selected from the group consisting of glass capillaries, alumina, silica, a chemically bonded hydrocarbon on silica, a polyolefin, agarose, a polysaccharide, or a glycoprotein; and
  ii) selectively reacts with one enantiomer in the enantiomeric mixture to form an enantiomeric derivative; and
b) separating the enantiomeric derivative from the enantiomeric mixture.

3. An apparatus for reacting one enantiomer, called the "reactive enantiomer," in an enantiomeric mixture, comprising:
a) a reaction vessel which contains an activated solid support in the form of particles and composed of a material selected from the group consisting of glass capillaries, alumina, silica, a chemically bonded hydrocarbon on silica, a polyolefin, agarose, a polysaccharide, or a glycoprotein, said reaction vessel having a solvent inlet and a solvent outlet plugged with a porous material wherein the pore size is smaller than the solid support;
b) means for introducing a sample into the reaction vessel connected to the solvent inlet of the reaction vessel;
c) means for feeding a solvent into the reaction vessel through the solvent inlet;
d) a sample collector connected to the outlet of the reaction vessel;
e) a separation means having a solvent inlet that is connected to the solvent outlet of the reaction vessel and a solvent outlet; and
f) a detector having an inlet connected from the solvent outlet of the separation means and a solvent outlet connected to the sample collector.

4. The apparatus of claim 3 further comprising:
a) a chiral detector having a solvent inlet connected from the outlet of the first reaction vessel and a solvent outlet; and
b) a valve which alternatively connects the outlet of the chiral detector to the inlet of the reaction vessel or connects the outlet of the reaction vessel to the separation means depending on the degree of conversion of the reactive enantiomer detected by the chiral detector.

5. The apparatus of claim 3 further comprising:
a) a chiral detector having a solvent inlet connected from the outlet of the reaction vessel and a solvent outlet;
b) a second reaction vessel which contains an activated solid support in the form of particles and composed of a material selected from the group consisting of glass capillaries, alumina, silica, a chemically bonded hydrocarbon on silica, a polyolefin, agarose, a polysaccharide, or a glycoprotein, said second reaction vessel having a solvent inlet and a solvent outlet plugged with a porous material wherein the pore size is smaller than the particle size of the solid support, and wherein the solvent outlet is connected to the separation means;
c) a valve which, alternatively, connects the outlet of the chiral detector to the inlet of the second reaction vessel or connects the outlet of the reaction vessel to the separation means depending on the degree of conversion of the reactive enantiomer detected by the chiral detector.

6. The apparatus of claim 5 wherein the separation means is selected from the group consisting of a reversed phase chromatography column, a normal phase chromatography column, an ion-exchange chromatography column, a gas chromatography column and an affinity chromatography column.

7. The apparatus of claim 6 wherein the separating means is a reversed phase column.

8. The apparatus of claim 6 wherein the separating means has multiple columns.

9. The apparatus of claim 6 wherein the separating means is a simulated moving bed apparatus.

10. The apparatus of claim 5 wherein the detector is selected from the group consisting of a ultraviolet light detector and a refractive index detector.

11. The apparatus of claim 5 wherein the means for feeding a solvent is selected from the group consisting of a pump, pressure from a compressed inert gas and gravity.

* * * * *

UNITED STATES PATENT AND TRADEMARK OFFICE
CERTIFICATE OF CORRECTION

PATENT NO.   : 6,461,858 B1  
DATED        : October 8, 2002  
INVENTOR(S)  : Richard L. Gabriel and David A. Swanson It is certified that error appears in the above-identified patent and that said Letters Patent is hereby corrected as shown below:

Title page,
Item [73], Assignee, please delete "Pharm-Eco Laboratories, Inc., Devens, MA (US)" and insert -- Johnson Matthey Pharmaceutical Materials, Inc., Devens, MA (US) --

Signed and Sealed this

Twelfth Day of August, 2003

JAMES E. ROGAN
*Director of the United States Patent and Trademark Office*

UNITED STATES PATENT AND TRADEMARK OFFICE
CERTIFICATE OF CORRECTION

| | |
|---|---|
| PATENT NO. | : 6,461,858 B1 |
| APPLICATION NO. | : 09/237334 |
| DATED | : October 8, 2002 |
| INVENTOR(S) | : Richard L. Gabriel and David A. Swanson |

Page 1 of 1

It is certified that error appears in the above-identified patent and that said Letters Patent is hereby corrected as shown below:

On Title Page, Item (56) under References Cited,
add --5,292,646  3/1994  Kosugi et al.-- and
--5,278,070  1/1994  Shum--

Signed and Sealed this

Sixth Day of February, 2007

JON W. DUDAS
*Director of the United States Patent and Trademark Office*